(12) United States Patent
Smolak et al.

(10) Patent No.: US 7,691,919 B2
(45) Date of Patent: Apr. 6, 2010

(54) DENTAL MATERIALS BASED ON ROMP COMPOSITES

(75) Inventors: Sonja Smolak, Munich (DE); Franz Stelzer, Graz (AT); Norbert Moszner, Eschen (LI); Volker M. Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 696 days.

(21) Appl. No.: 10/934,904

(22) Filed: Sep. 3, 2004

(65) Prior Publication Data
US 2005/0159510 A1 Jul. 21, 2005

(30) Foreign Application Priority Data
Jan. 15, 2004 (DE) .................. 10 2004 002 178

(51) Int. Cl.
*A61K 6/083* (2006.01)
*A61K 6/02* (2006.01)
*A61K 6/08* (2006.01)
*C08K 9/12* (2006.01)
*A61C 5/00* (2006.01)
*C08F 32/00* (2006.01)

(52) U.S. Cl. .................. 523/115; 523/116; 523/118; 523/210; 523/117; 433/228.1; 526/280; 526/281

(58) Field of Classification Search .................. 526/171, 526/279, 348, 280, 281, 318, 317.1; 523/216, 523/116, 115, 118, 210, 117; 433/228.1
See application file for complete search history.

(56) References Cited

U.S. PATENT DOCUMENTS

| | | | |
|---|---|---|---|
| 4,387,215 A | | 6/1983 | Bailey |
| 5,455,489 A | * | 10/1995 | Bhargava .................. 315/169.4 |
| 5,665,839 A | | 9/1997 | Rizzardo et al. |
| 6,001,909 A | * | 12/1999 | Setiabudi .................. 524/265 |
| 6,147,136 A | * | 11/2000 | Bissinger .................. 523/116 |
| 6,455,029 B1 | | 9/2002 | Angeletakis et al. |
| 6,479,592 B2 | * | 11/2002 | Rheinberger et al. ........ 525/205 |
| 6,555,255 B2 | * | 4/2003 | Barton et al. .............. 428/690 |

(Continued)

FOREIGN PATENT DOCUMENTS

DE 44 39 485 A1 5/1996

(Continued)

OTHER PUBLICATIONS

Kanaoka, S.; Grubbs, R. H. Synthesis of Block Copolymers of Silicon-Containing Norbornene Derivatives via Living Ring-Opening Metathesis Polymerization Catalyzed by a Ruthenium Carbene Complex, Macromolecules, 1995, 28, 4707-4713. American Chemical Society.*

(Continued)

*Primary Examiner*—Mark Eashoo
*Assistant Examiner*—Michael Pepitone
(74) *Attorney, Agent, or Firm*—Nixon & Peabody LLP

(57) ABSTRACT

The invention relates to compositions, polymerizable by ring-opening metathesis, which contain (a) at least one monomer and/or oligomer which is polymerizable by ring-opening metathesis polymerization, (b) at least one filler and (c) at least one initiator for the ring-opening metathesis polymerization. The compositions are characterized in that the initiator is chemically or physically bound to the filler.

16 Claims, 2 Drawing Sheets

U.S. PATENT DOCUMENTS

| | | | |
|---|---|---|---|
| 6,660,813 B2* | 12/2003 | Wagener et al. | 526/71 |
| 7,022,410 B2* | 4/2006 | Tonapi et al. | 428/414 |
| 7,252,883 B2 | 8/2007 | Wakiya et al. | |
| 2002/0071813 A1* | 6/2002 | Angeletakis et al. | 424/49 |
| 2002/0107138 A1* | 8/2002 | Hoveyda et al. | 502/152 |
| 2002/0143118 A1* | 10/2002 | Rheinberger et al. | 526/72 |
| 2002/0167100 A1* | 11/2002 | Moszner et al. | 264/16 |
| 2003/0144437 A1* | 7/2003 | Bell et al. | 526/171 |
| 2004/0068075 A1* | 4/2004 | Lichtenhan et al. | 528/15 |
| 2004/0225073 A1* | 11/2004 | Angeletakis | 525/342 |
| 2005/0043541 A1* | 2/2005 | Walter et al. | 548/101 |
| 2006/0024436 A1* | 2/2006 | Bayya et al. | 427/212 |

FOREIGN PATENT DOCUMENTS

| | | |
|---|---|---|
| DE | 195 06 222 A1 | 8/1996 |
| DE | 196 08 316 A1 | 8/1997 |
| DE | 196 12 004 A1 | 10/1997 |
| DE | 199 05 093 A1 | 8/2000 |
| EP | 0 796 607 A2 | 9/1997 |
| EP | 864595 A1 * | 9/1998 |
| EP | 0 904 766 A2 | 3/1999 |
| EP | 0 904 767 A2 | 3/1999 |
| JP | 3-153727 | 7/1991 |
| WO | WO 94/00501 | 1/1997 |
| WO | WO 97/06185 | 2/1997 |
| WO | WO 99/00397 | 1/1999 |
| WO | WO 00/61288 | 10/2000 |
| WO | WO 00/71554 | 11/2000 |
| WO | WO 02/14376 | 2/2002 |

OTHER PUBLICATIONS

Schrock, R. R.; Living Ring-Opening Metathesis Polymerization Catalyzed by Well-Characterized Transition-Metal Alkylidene Complexes, Acc. Chem. Res. 1990, 23, 158-165. American Chemical Society.*

Kim, Y. N. et al. Surface-Initiated Ring-opening Metathesis Polymerization on Si/SiO2; Macromolecules, 2000, 33, 2793-2795. American Chemical Society.*

Jordi et al., "The Preparation of Silica-Poly(Norbornene) Nanocomposites by Surface Initiated Polymerization," *Polymer Reprints* 44(1):542-543 (2003).

Barrett et al., "ROMP-Spheres: A Novel High-Loading Polymer Support Using Cross Metathesis Between Vinyl Polystyrene and Norbornene Derivatives," *Organic Letters* 1(7):1083-1086 (1999).

Buchmeiser et al., "Ring-Opening Metathesis Polymerization for the Preparation of Surface-Grafted Polymer Supports," *Macromolecules* 33:32-39 (2000).

Kim et al., "Surface-Initiated Ring-Opening Metathesis Polymerization on Si/SiO$_2$," *Macromolecules* 33:2793-2795 (2000).

Fürstner et al., "Ruthenium Carbene Complexes with N,N-Bis(mesityl)imidazol-2-ylidene Ligands: RCM Catalysts of Extended Scope," *J. Org. Chem.* 65:2204-2207 (2000).

Garber et al., "Efficient and Recyclable Monomeric and Dendritic Ru-Based Metathesis Catalysts," *J. Am. Chem. Soc.* 122:8168-8179 (2000).

Hafner et al., "Einkomponentige Katalysatoren für die thermische und photoinduzierte Ringöffnungs-Metathese-Polymerisation," *Angew. Chem.* 109(19):2213-2216 (1997).

Jafarpour et al., "Indenylidene-Imidazolylidene Complexes of Ruthenium as Ring-Closing Metathesis Catalysts," *Organometallics* 18:5416-5419 (1999).

Kingsbury et al., "A Recyclable Ru-Based Metathesis Catalyst," *J. Am. Chem. Soc.* 121:791-799 (1999).

Love et al., "A Practical and Highly Active Ruthenium-Based Catalyst that Effects the Cross Metathesis of Acrylonitrile," *Angew. Chem.* 114(21):4207-4209 (2002).

Nguyen et al., "Ring-Opening Metathesis Polymerization (ROMP) of Norbornene by a Group VIII Carbene Complex in Protic Media," *J. Am. Chem. Soc.* 114:3974-3975 (1992).

Sanford et al., "A Versatile Precursor for the Synthesis of New Ruthenium Olefin Metathesis Catalysts," *Organometallics* 20:5314-5318 (2001).

Scholl et al., "Increased Ring Closing Metathesis Activity of Ruthenium-Based Olefin Metathesis Catalysts Coordinated with Imidazolin-2-ylidene Ligands," *Tetrahedron Letters* 40:2247-2250 (1999).

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," *Organic Letters* 1(6):953-956 (1999).

Schwab et al., "Synthesis and Applications of RuCl$_2$(=CHR')(PR$_3$)$_2$: The Influence of the Alkylidene Moiety on Metathesis Activity," *J. Am. Chem. Soc.* 118:100-110 (1996).

Van Der Voort et al., "Silylation of the Silica Surface. A Review," *J. Liq. Chrom. & Rel. Technol.* 19(17&18):2723-2752 (1996).

Weskamp et al., "N-heterocyclic Carabenes: Novel Ruthenium-Alkylidene Complexes," *Journal of Organometallic Chemistry* 582:362-365 (1999).

Yao, "Ein löslicher, polymergebundener Rutheniumcarbenkomplex: ein robuster und wiederverwendbarer Katalysator für Ringschluss-Olefinmetathesen." *Angew. Chem.* 112(21):4060-4062 (2000).

van der Schaaf et al., "Synthesis and Reactivity of Novel Ruthenium Carbene Atalysts. X-ray Structures of [RuCl$_2$(=CHSC$_6$H$_5$)(P'Pr$_3$)$_2$] and [RuCl$_2$(CHCH$_2$CH$_2$-C,N-2-C$_5$H$_4$N(P'Pr$_3$)]," *Journal of Organometallic Chemistry*, 606:65-74 (2000).

Delaude et al., "Visible Light Induced Ring-Opening Metathesis Polymerisation of Cyclooctene," *Chem. Commun.*, 986-987 (2001).

Schürer et al., "Synthese und Anwendung eines permanent immobilisierten Olefinmetathese-Katalysators," *Angew. Chem.*, 112:4062-4065 (2000).

Fürstner et al., "Olefinmetathese und mehr," *Angew. Chem.*, 112:3141-3172 (2000).

Yoshida et al., "Multilayer Alkoxysilane Silylation of Oxide Surfaces," *Langmuir*, 17:5882-5888 (2001).

Examination Report for Japanese Patent Application 2005-6915 (Jul. 10, 2009).

* cited by examiner

DENTAL MATERIALS BASED ON ROMP COMPOSITES

The present invention relates to filler-containing compositions based on monomers which can be polymerized by ring-opening metathesis. The compositions contain an initiator for the ring-opening metathesis polymerization which is chemically or physically bound to the filler, and are suitable in particular as dental materials.

The polymerization of monomers and monomer mixtures in most cases involves a lesser or greater degree of volume contraction. This polymerization shrinkage has a disadvantageous effect on the dimensional stability and the mechanical properties of shaped parts. In the case of adhesives and gluing compounds it adversely effects the adhesion properties and composite strength, which in the case of dental materials encourages the development of gaps between tooth and filling and thus the formation of secondary caries.

Ring-opening polymerization generally involves a low polymerization shrinkage, and many attempts have therefore been made to make this usable for the preparation of dental materials.

U.S. Pat. No. 4,387,215 discloses spiroorthoesters, spiroorthocarbonates and polycyclic ketal lactones which can be polymerized in ring-opening manner and which, during polymerization, are said not to shrink and sometimes even to expand.

WO 94/00501 describes a process for the preparation of polymers which contain repeating spiroorthoester groups and are said to be suitable for the preparation of dental materials.

DE 195 06 222 A1 discloses cationically polymerizable, low-shrinkage materials for medical applications and dental purposes based on the basis of oxetane and oxacyclobutane derivatives.

DE 44 39 485 C2 relates to bicycloaliphatic 2-methylene-1,3-dioxepanes which can be radically and cationically polymerized.

In U.S. Pat. No. 5,665,839 radically polymerizable oxathiepanes are described which permit the preparation of polymers with ester, amide or thioester groups.

DE 196 12 004 A1 discloses multifunctional vinylcyclopropane derivatives which are suitable in particular for the preparation of dental materials. The vinylcyclopropanes can be radically polymerized and form polymers without hydrolytically splitting groups in the main chain.

A feature common to the above monomers is that their synthesis is elaborate and expensive. Moreover monomers such as spiroorthocarbonates, spiroorthoesters or 2-methylene-1,3-dioxepanes are moisture-sensitive and have only a limited stability at room temperature and in the presence of $SiO_2$ or siliceous fillers.

DE 196 08 316 A1 relates to norbornenyl derivatives substituted by (meth)acrylate groups which can be polymerized by ring-opening metathesis polymerization (ROMP) and are suitable in particular for the preparation of dental materials.

Functionalized polymers are known from EP 0 796 607 A2 which are accessible by ring-opening metathesis polymerization of norbornene derivatives. These polymers contain carboxylic acid groups and polymerizable groups and can be crosslinked by radical polymerization. The polymers are suitable for the preparation of adhesives and coating materials and can form composite cements with ion-releasing fillers.

EP 0 904 766 A2 discloses dental compositions curable by ROMP based on monomers with unsaturated cyclic or polycyclic radicals, a filler and an initiator for the ring-opening metathesis polymerization. The materials are said to be characterized by rapid polymerization and a small volume shrinkage.

EP 0 904 767 A2 relates to dental materials based on oligomers and polymers which can be obtained for their part by ring-opening metathesis polymerization.

DE 199 05 093 A1 discloses storage-stable and moisture-insensitive dental materials based on bicyclic ring systems such as e.g. bicyclo[2.2.1]heptene derivatives which can be polymerized by ROMP.

In U.S. Pat. No. 6,455,029 impression materials are described, which contain telechelic oligomers or polymers curable by ROMP, functionalized with norbornenyl groups, based on polydimethylsiloxane.

WO 00/61288 discloses functionalized supporting materials for chromatographic applications which are accessible by derivatization of organic or inorganic supports with polymerizable groups. The polymerizable groups are reacted with a monomer open to metathesis polymerization in the course of a graft polymerization. The monomer contains groups or substituents which are responsible for the chromatographic separation characteristics.

Immobilized metathesis catalysts are known from WO 02/14376 which are to be easily separable from the reaction medium. A typical application field for these catalysts are ring-forming metathesis reactions.

Schürer et al., Angew. Chem. 2000, 112, 4062, disclose a polymer-bound metathesis initiator for ring-closure metathesis which is easily separable from the reaction solution and can also be re-used. Compared with unbounded catalysts a lower level of activity was found, for which diffusion problems to the active centre are responsible. No polymerizations with this initiator have been described.

In an overview article A. Fürstner, *Angew. Chem.* 2000, 112, 3140-3172, deals with olefin metathesis. He confirms the lower level of activity of immobilized catalysts.

A basic problem of ring-opening metathesis polymerization is to be seen in the fact that the initiators used are only poorly soluble in liquid, ROMP-polymerizable monomers, which makes a homogeneous distribution of the initiators difficult and thus leads to inhomogenities on the one hand and makes greater initiator quantities necessary on the other hand. As metathesis initiators are mostly intensely coloured compounds, coloured materials are included which are unsuitable for dental applications, particularly in visible areas.

Moreover, the resistance to moisture of conventional materials curable by ROMP is not satisfactory, as a deterioration of the mechanical properties caused by interstitial water is often observed.

The object of the invention is to provide filler-containing materials which can be cured by ring-opening metathesis polymerization without displaying the above disadvantages and which are suitable in particular for use as dental materials.

This object is achieved according to the invention by compositions which contain (a) at least one monomer and/or oligomer which is polymerizable by ring-opening metathesis polymerization, (b) at least one filler, and (c) at least one initiator for ring-opening metathesis polymerization.

The compositions are characterized in that the initiator is bound to the filler in chemical or physical form.

Variant B shows an adsorptively bound, thermally activatable initiator. The filler surface is modified with a silane, which carries a group capable of metathesis. During the thermal activation this reacts with the initiator, the latter being covalently bound to the filler surface.

Figure 2:
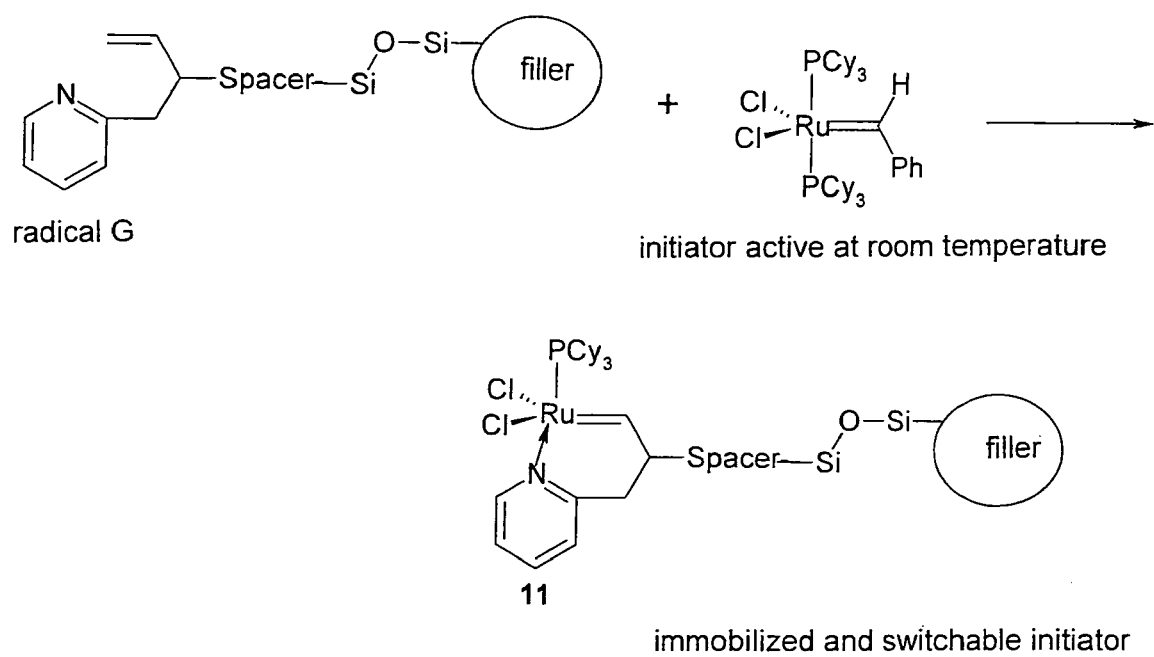

FIG. 2 schematically shows an activatable, covalently bound initiator.

To prepare compositions according to the invention the filler is preferably treated with a binder which serves to bind the initiator to the filler. The filler is then charged with the initiator which is bound to the filler by covalent or physical interactions. Finally the initiator-charged filler is mixed with monomer. The described sequence of the process steps is not obligatory. For example the initiator can also firstly be reacted with a suitable binder and then bound to the filler.

Compositions which contain filler and a polymerizable or polymeric matrix material are also called composites.

According to a preferred version the initiator is bound to the filler using a silane of formula (1):

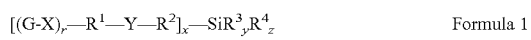

Formula 1 in which the variables have the following meanings:

G=a linear or branched organic radical capable of metathesis with m carbon atoms, m being an integer from 1 to 40, and 0 to (m−2) heteroatoms, selected from N, O, Si, P and S, or a cyclic or polycyclic, cycloaliphatic or aromatic organic radical capable of metathesis with m' carbon atoms, m' being an integer from 3 to 63, and 0 to (m'−2) heteroatoms, selected from N, O, Si, P and S.

The above-defined aliphatic groups G preferably contain 15 heteroatoms at most, the cyclic groups G 28 heteroatoms at most, provided that, according to the above definition, such a number of heteroatoms is possible.

The carbon atoms and heteroatoms of group G can form 1 to (m−2) carbonyl groups in the case of aliphatic groups or 1 to (m'−2) carbonyl groups in the case of cyclic groups. The maximum number of carbonyl groups is preferably 10 at most for aliphatic groups, preferably 15 at most for cyclic groups, provided that, according to the above definitions, there is a corresponding number of carbon atoms and heteroatoms.

X,Y=independently of each other —(C(=O)—O—, —C(=O)—N—, —O—C(=O)—O—, —O—C(=O)—NR$^5$—, —CR$^5$=N—, —O—, —S—, with R$^5$=H, C$_1$-C$_6$ alkyl, benzyl or is absent;

R$^1$=a (r+1)-valent, linear or branched aliphatic, cycloaliphatic or aromatic organic radical C$_2$-C$_{10}$ radical or is absent;

R$^2$=a C$_1$-C$_5$ alkylene group or is absent;

R$^3$=halogen, hydroxy, a C$_1$-C$_5$ alkoxy- or C$_1$-C$_5$ acyloxy group;

R$^4$=C$_1$-C$_{12}$ alkyl, C$_3$-C$_{12}$ cyloalkyl or phenyl;

r=1, 2 or 3;

x=1, 2 or 3;

y=1, 2 or 3;

z=0, 1 or 2, the sum of the variables x+y+z equalling 4.

By halogen is meant, unless otherwise stated, preferably chlorine, bromine or iodine.

Suitable as groups G capable of metathesis are unsaturated groups, which preferably contain terminal C—C-double- or C—C-triple bonds, such as e.g. vinyl, allyl or alkinyl groups, preferably unsaturated cyclic groups such as e.g. cyclooctenyl or particularly preferably norbornenyl groups. (Meth) acrylate groups are not suitable, however.

Silanes of formula (1) are particularly preferred, in which the variables have the following meanings:

G=a radical of formula (2)

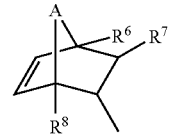

Formula (2)

in which the variables are defined as follows:

A=O, NH, S, a saturated or unsaturated organic radical with t carbon atoms, t being an integer from 1 to 12, which can contain 0 to (t−1) heteroatoms, selected from N, O, Si, P and S;

R$^6$, R$^7$, R$^8$=independently of each other in each case a linear or branched aliphatic radical with q carbon atoms, q being an integer from 1 to 15, a cyclic or polycyclic organic radical with q' carbon atoms, q' being an integer from 3 to 15, and 0 to (q−1) or 0 to (q'−1) heteroatoms, selected from N, O, Si, P, and S;

X,Y=are absent;

R$^1$=a linear C$_1$- to C$_5$ alkylene radical or is absent;

R$^2$=is absent;

R$^3$=chlorine, methoxy, ethoxy;

R$^4$=methyl;

r=1;

x=1;

y=1, 2 or 3;

z=0, 1 or 2;

the sum of x+y+z equalling 4.

A and independently thereof R$^6$, R$^7$, R$^8$ preferably contain 7 heteroatoms at most, provided that the above definitions permit such a number of heteroatoms.

The carbon atoms and heteroatoms of R$^6$, R$^7$, R$^8$ can form 1 to (q−1) and (q'−1) carbonyl groups respectively. The maximum number of carbonyl groups is preferably 5 at most, provided that the above definitions permit such a number of carbon atoms and heteroatoms.

The preferred meanings of the individual variables can be selected independently of each other. Silanes in which 2 or more, preferably all, of the variables have one of the preferred meanings are naturally quite particularly preferred.

Accordingly, particularly preferred compounds of formula 1 are norborn-2-ene-5-yl-trichlorosilane, norborn-2-ene-5-yl-triethoxysilane, norborn-2-ene-5-yl-dimethylchlorosilane, norborn-2-ene-5-yl-dimethylethoxysilane, norborn-2-ene-5-yl-methyldichlorosilane and norborn-2-ene-5-yl-methyldiethoxysilane.

According to a further embodiment the initiator is physically bound to the filler. To this end the filler is preferably treated with a silane which contains no groups capable of metathesis. The physical bond takes place using a silane of formula (3), in which the variables have the following meanings:

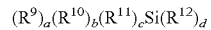

Formula (3)

$R^{12}$=halogen, hydroxy, a $C_1$-$C_5$ alkoxy or $C_1$-$C_5$ acyloxy group;

$R^9$, $R^{10}$, $R^{11}$=independently of each other a saturated or unsaturated, linear or branched organic radical with s carbon atoms, s being an integer from 2 to 20, and 0 to (s−1) heteroatoms, selected from N, O, Si, P and S; or
 a saturated, unsaturated or aromatic, cyclic or polycyclic organic radical with s' carbon atoms, s' being an integer from 3 to 15, with 0 to (s'−1) heteroatoms, selected from N, O, Si, P and S;

a=0, 1, 2 or 3;
b=0, 1, 2 or 3;
c=0, 1, 2 or 3;
d=1, 2 or 3

The sum of a+b+c+d is 4.

The radicals $R^9$, $R^{10}$, $R^{11}$ preferably contain 7 heteroatoms at most, provided that the above definitions permit such a number of heteroatoms.

The carbon atoms and heteroatoms of $R^9$, $R^{10}$, $R^{11}$ can form 1 to (s−1) and (s'−1) carbonyl groups respectively. The maximum number of carbonyl groups is preferably 5 at most, provided that the above definitions permit such a number of carbon atoms and heteroatoms.

Preferred radicals for $R^9$, $R^{10}$, $R^{11}$ are, independently of each other, methyl, ethyl, propyl, cyclohexyl or phenyl.

Particularly preferred silanes of formula (3) are compounds, which, along with halogen radicals or alkoxy groups, carry exclusively alkyl radicals, such as trimethylchlorosilane or trimethylalkoxysilane.

The silanes of formula (1) make possible a physical or chemical bond of the initiator to the filler surface. The silanes react on the one hand with splitting-off of $R^3$ with hydroxyl groups of the filler surface and on the other hand via the groups capable of metathesis with the initiator, so that this is covalently bound to the filler. Initiators which are active at room temperature already react when the filler is being charged with the groups capable of metathesis. Photochemically or thermally activatable initiators are adsorbed at the filler surface. The reaction with the groups of the filler surface that are capable of metathesis takes place in this case only after the corresponding activation.

Preferred as fillers are the inorganic particulate fillers used in dentistry, e.g. powders of X-ray opaque glasses or highly-dispersed silicic acid. For the dental materials according to the invention it is above all inorganic particulate fillers, such as microfine fillers with a primary particle size of 5.0 to 500 nm, e.g. pyrogenic silicic acid or precipitated silicic acid or mixed oxides of $SiO_2$, $ZrO_2$, $TaO_2$, $La_2O_3$, $Yb_2O_3$ and/or $CeO_2$, as well as macro- or minifillers with an average particle size of 0.01 to 5 μm, such as quartz, glass ceramic or glass powders, as well as X-ray opaque fillers, such as ytterbium trifluoride, that can be used as fillers.

The surface modification of the fillers is carried out in the case of the above described silanes in suspension in a dry organic solvent, e.g. toluene or xylene. The hydrolytic cleavage products are removed from the reaction mixture e.g. by adding tertiary amines as acid scavengers when using chlorosilanes. When using alkoxysilanes the resulting alcohol is removed by distillation from the reaction mixture. For processing, the modified filler is centrifuged off, washed and dried in vacuum.

The bond of the silanes to the filler takes place, after hydrolysis of the labile silicon-chlorine or silicon-alkoxy-bond by surface-adsorbed water to silanols, in a condensation reaction with the silanol groups of the filler (P. van der Voort, E. F. Vansant, J. Liqu. Chrom. Rel. Technol. 1996, 19, 2723).

The quantity of silanization agents is preferably chosen such that the level of groups capable of metathesis in the filler is 0.0001-1.0 mmol per gram of filler and particularly preferably 0.01-0.3 mmol per gram of filler. The maximum quantity of silanization agent per gram of filler is determined by the specific surface of the filler and its $SiO_2$ content. The greater the specific surface or the $SiO_2$ content, the more Si—OH groups are present and the more silanization agents can be bound.

In the case of pure $SiO_2$ the specific surface is preferably 20 and 200 m²/g, $SiO_2$ with a specific surface of 40 to 100 m²/g being particularly preferred. In the case of $SiO_2$-containing glasses the $SiO_2$ content is preferably 10 and 95 wt.-%, an $SiO_2$ content between 30 and 60 wt.-% being particularly preferred.

The extent of the silanization can be determined using C,H elemental analysis.

Figure 1:
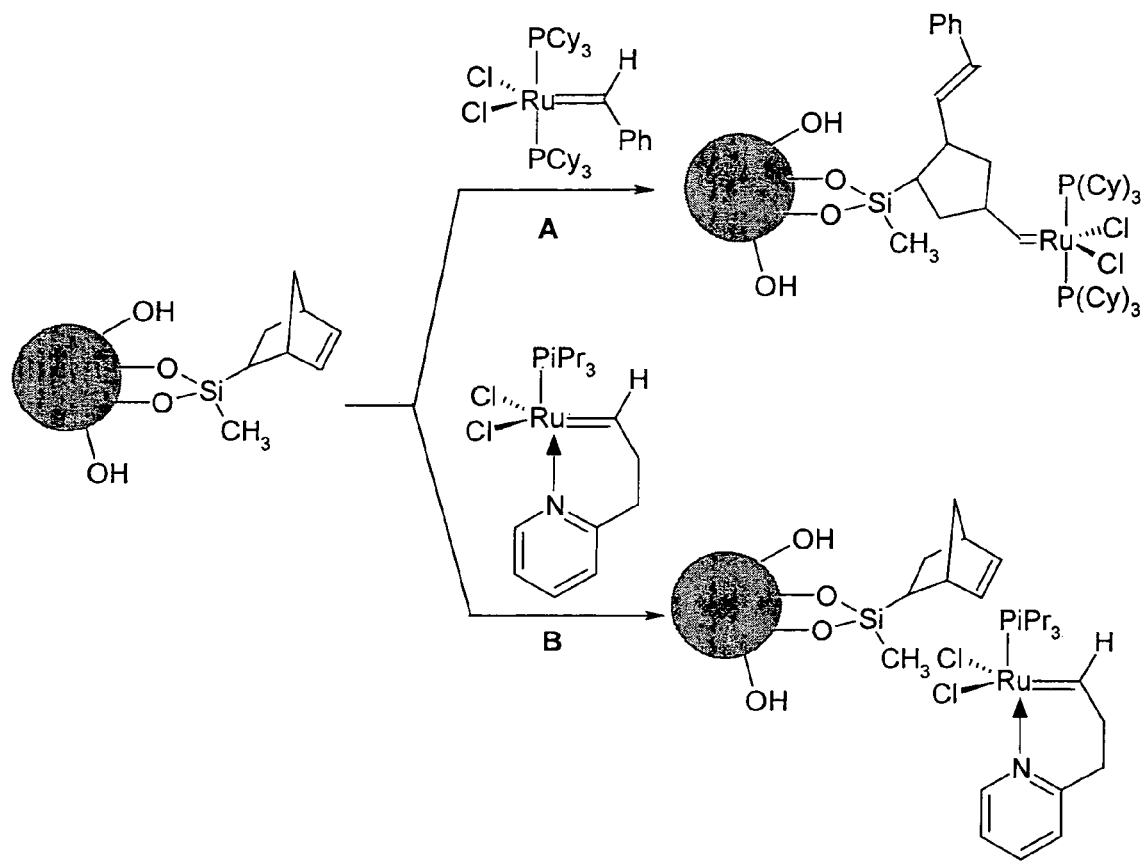
FIG. 1 schematically shows the binding of a ROMP initiator to a support. Variant A shows a covalently bound initiator.

The surface-modified filler is charged with a metathesis initiator. The metathesis initiator can be an initiator already active at room temperature, e.g. a transition metal carbene active at room temperature. In this case the initiator already reacts upon mixing with the groups of the filler surface capable of metathesis reaction and is covalently bound to the filler, as is shown in FIG. 1, variant A. It is assumed here that the mixing of the components normally takes place at room temperature.

Upon the addition of the monomer the polymerization starts off from the filler surface, the initiator still remaining at the end of the growing polymer chain. In the case of thermally or photochemically activatable initiators the polymerization starts only after activation.

Preferred initiators active at room temperature are those according to general formula 4, in which the variables have the following meanings:

Formula 4

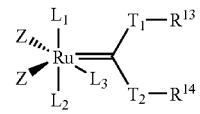

Z=Cl, Br, F, I, tosylate or one of the meanings given for $L_1$, $L_2$, $L_3$;

$L_1$, $L_2$, $L_3$=independently of each other $P(R^{15})_3$ with $R^{15}$=phenyl, isopropyl, cyclohexyl or

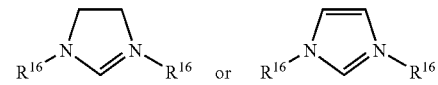

with $R^{16}$=mesityl (2,4,6-trimethylphenyl; MES).
 or pyridine which is unsubstituted or substituted in position 2 or in positions 2 and 4 with Br, Cl, F, I, $OCH_3$;
 or is absent;

$R^{13}$, $R^{14}$=independently of each other H or an aromatic or aliphatic, polycyclic or condensed $C_6$-$C_{20}$ ring or ring system, with 0-5 heteroatoms in the ring, selected from N, S, O, P, the ring or the ring system being unsubstituted or being additionally substituted with 0-5 substituents selected from —Cl, —Br, —I, —F, —$OR^{17}$, —CH=N—$R^{17}$, —C(=O)$R^{17}$, —C(=O)$OR^{17}$, —OC(=O)$R^{17}$, $R^{17}$ being a linear or branched, acyclic $C_1$-$C_{14}$ alkyl or cyclic $C_3$-$C_{14}$ alkyl or an aromatic radical with 6 to 14 carbon atoms, $R^{17}$ being able to contain 0-5 heteroatoms, selected from N, O, Si, S;

$T_1$, $T_2$=independently of each other —O—, —S—, or a saturated $C_1$ to $C_4$ alkylene or unsaturated $C_2$ to $C_4$ alkylene which can additionally contain 0-2 heteroatoms of the group N, O, S, Si or is absent.

Particularly preferred metathesis initiators active at room temperature are the following compounds:

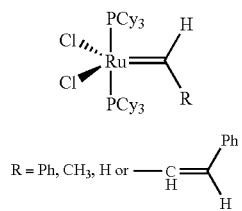

1

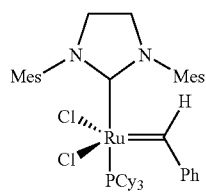

2

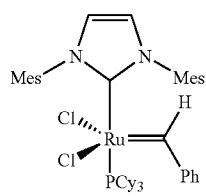

3

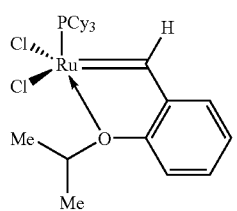

4

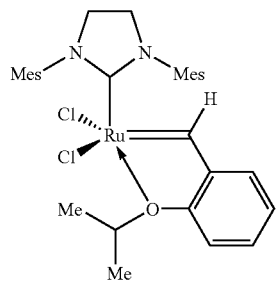

5

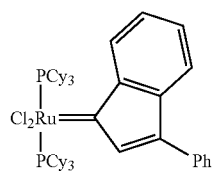

6

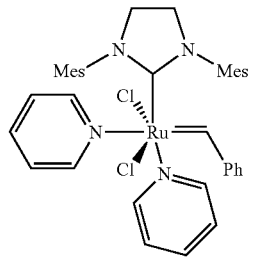

7

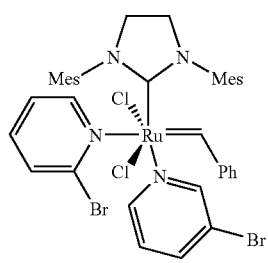

8

Cy = Cyclohexyl; Me = Methyl; MES = 2, 4, 6-Trimethylphenyl

These initiators are already known from the literature: 1: T. S. Nguyen, L. K. Johnson, R. H. Grubbs, J. W. Ziller; J. Am. Chem. Soc. 1992, 114, 3974; P. Schwab, R. H. Grubbs, J. W. Ziller, J. Am. Chem. Soc. 1996, 118, 100; WO9706185. 2: M. Scholl, S. Ding, C. W. Lee, R. H. Grubbs, Org. Lett. 1999, 953; WO0071554. 3: M. Scholl, T. M. Trnka, J. P. Morgan, R. H. Grubbs, Tetrahedron. Lett. 1999, 40, 2247; T. Weskamp, F. J. Kohl, W. Hieringer, D. Gleich, W. A. Hermann, J. Organomet. Chem. 1999, 582, 362. 4: J. S. Kingsbury, J. P. A. Harrity, P. J. Bonitatebus, A. H. Hoveyda, J. Am. Chem. Soc. 1999, 121, 791. 5: S. B. Garber, J. S. Kingsbury, B. Gray, A. H. Hoveyda, J. Am. Chem. Soc. 2000, 122, 8168; WO0214376. 6: L. Jafarpour, H.-J. Schanz, E. D. Stevens, S. P. Nolan, Organometallics 1999, 18, 5416; A. Fürstner, O. R. Thiel, L. Ackermann, H.-J. Schanz, S. P. Nolan, J. Org. Chem. 2000, 65, 2204. 7: M. S. Sanford, J. A. Love, R. H. Grubbs, Organometallics, 2001, 20, 5314. 8: J. A. Love, J. P. Morgan, T. M. Trnka, R. H. Grubbs, Angew. Chem., 2002, 114, 4207. The initiators 1, 2, 4 and 5 are commercially available from Materia Inc., Pasadena.

The compositions according to the invention preferably contain an initiator for the ROMP which can be thermally or photochemically activated.

Preferred thermally and/or photochemically activatable initiators are those according to general formula 5, in which the variables have the following meanings:

Formula 5

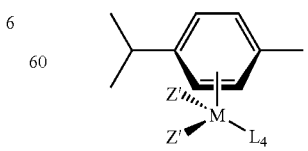

M=Os or Ru;

Z'=Cl, Br, F, I, tosylate or one of the meanings given for $L_4$;

$L_4=P(R^{18})_3$ with $R^{18}$=phenyl, isopropyl, cyclohexyl or

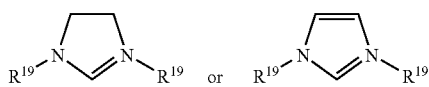

with $R^{19}$=mesityl (2,4,6-trimethylphenyl).

Further preferred thermally or photochemically active metathesis initiators are the following compounds:

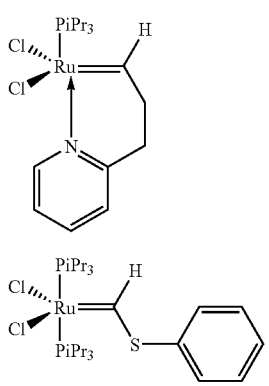

The initiators 9 and 10 can be thermally, and initiators of the formula 5 photochemically and thermally, initiated. These initiators are already known from the literature: 9 and 10: P. A. van der Schaaf, R. Kolly, H-J. Kirner, F. Rime, A. Mühlebach, A. Hafner, J. Organometallic Chem., 2000, 606, 65; WO99/00397; formula 5: A. Hafner, A. Mühlebach, P. A. van der Schaaf, Angew. Chem. 1997, 109, 2213; L. Delaude, A. Demonceau, A. F. Noels, Chem. Commun, 2001, 986.

Thermally or photochemically switchable initiators such as e.g. thermo- or photolabile compounds of type 9, 10 or formula 5 are initially adsorbed only at the filler surface, and not covalently bound. The filler modified with groups capable of metathesis is so to speak surface-impregnated with the metathesis initiator, as shown in FIG. 1, variant B. The initiator molecules are located however in the immediate vicinity of the reactive, functional groups of the filler. If these fillers impregnated with initiator are mixed with ROMP-capable monomer and the switchable metathesis initiator is activated by supplying heat or light, the metathesis polymerization starts. Through the physical closeness of the adsorbed initiator molecules to the metathesis-active anchor groups of the filler these are incorporated into the polymer; eventually a covalent bond also results between inorganic filler and organic matrix.

It is also possible to bind the initiator to the filler via silanes according to formula (1) which, along with one or more groups G capable of metathesis, contain at least one group which can develop coordinate bonds to the metal centre of the initiator. In this way, switchable initiators covalently bound to the filler can be produced. For example an initiator active at room temperature such as 1 or 2, as shown in FIG. 2, can be bound via a metathesis reaction to the group capable of metathesis of the silanized filler. At the same time a functional group that is also present, e.g. a pyridinyl group, can displace a phosphine ligand and coordinate to the metal centre of the initiator. The thus-obtained initiator 11 is an immobilized analogon to the switchable initiator 9. It is possible in this way to immobilize an initiator active at room temperature at the filler and at the same time to convert it into a thermally or photochemically switchable form.

Within the present invention, both initiators which are immediately covalently bound to the filler and initiators which are covalently bound only after appropriate activation are called chemically bound initiators. By physically bound initiators are meant substances which are also not covalently bound to the filler after the materials are cured. Chemically bound initiators are preferred according to the invention.

The filler is charged with the initiator by suspending the filler, preferably filler which has been treated with a binder, at room temperature in a solution of the metathesis initiator in a dry organic solvent and stirring it. In the case of the metathesis initiators active at room temperature, stirring lasts until the initiator has completely reacted with the reactive filler and the solution is discoloured. The solvent is removed and the initiating filler is dried in vacuum and stored cooled under inert gas.

In the case of the thermally or photochemically activatable initiators the filler is suspended at room temperature in a solution of the switchable metathesis initiator, if necessary in darkness, stirred and the solvent drawn off under reduced pressure. The fillers charged with initiator are stored cooled under inert gas.

The solvents pentane, cyclohexane, heptane, toluene, xylene, dichloromethane, chloroform, chlorobenzene, acetone, THF and diethylether have proved particularly suitable for application of the initiator.

The charging of the filler with initiator is preferably between 0.00001 and 0.1 mmol, preferably 0.0001 to 0.05 mmol, and quite particularly preferably 0.001 to 0.01 mmol initiator per gram of filler.

According to the invention, preferably 10% at most, particularly preferably 2 to 10% of the groups capable of metathesis of the filler are charged by initiator.

Along with the filler charged with initiator, the compositions according to the invention can additionally contain a filler portion which does not carry an initiator. Particularly suitable as further fillers are materials which are modified with groups which are open to the ring-opening polymerization, preferably a silane of formula (1). Fillers with groups capable of metathesis act as crosslinkers during polymerization of the compositions and are covalently bound into the polymer network during the ROMP. The above-defined particulate inorganic materials are preferred as filler materials.

The use of initiator-free filler portions which are modified with groups capable of metathesis is preferred in particular if the initiator is bound to filler which is modified with a silane of formula (3), i.e. a silane without radicals capable of metathesis. Compositions which contain exclusively fillers which are modified with groups capable of metathesis polymerization, are particularly preferred however, as all the filler portions are thus covalently bound into the cured material during metathesis polymerization.

The filler charged with initiator is mixed with at least one monomer and/or oligomer which can be polymerized by ROMP.

In the case of the initiators active at room temperature, the polymerization already starts when the components are mixed, so that only two-component systems can be realized in which initiator-containing filler and ROMP monomer are distributed separately over two or more different components. Kits for the preparation of compositions according to the invention which contain initiator-containing filler and monomer/oligomer (a) in physically separated form are likewise the subject of the invention. Kits according to the invention can contain for example initiator-containing filler (component 1) and a low-viscosity paste of surface-modified filler and monomer/oligomer (component 2) or initiator-containing filler (component 1) and liquid monomer/oligomer or monomer/oligomer mixture (component 2).

In the case of thermally or photochemically switchable initiators, single-component systems are possible, i.e. a composite paste storage stable at room temperature made of initiating filler, optionally further filler and monomer/oligomer can be prepared. The curing of the mixture takes place only by supplying heat or irradiation with light.

Monomers or monomer mixtures are preferably used as component (a). Preferred as monomers are metathetically polymerizable ring systems, preferably bi- or multicyclic ring systems with at least one endocyclic double bond. Particularly suitable are carbocyclic and heterocyclic bicyclo[x',y', z']hydrocarbons, where x', y', z' independently of each other are in each case an integer from 1 to 6, preferably x'=2, y'=2, z'=1.

Particularly preferably used are norbornene derivatives of general formulae (6) and/or (7)

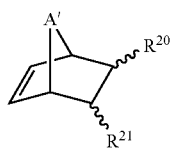

Formula (6)

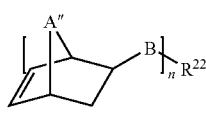

Formula (7)

in which the variables have the following meanings:
A', A''=O, S, NH, a saturated or unsaturated organic radical with u carbon atoms, u being an integer from 1 to 15, which can contain 0 to (u−1) heteroatoms, selected from N, O, Si, P and S;
B=—CH$_2$— or is absent;
R$^{20}$, R$^{21}$=H or a saturated or unsaturated organic radical with v carbon atoms, v being an integer from 1 to 30, and with 0 to (v−1) heteroatoms from the group N, O, Si, P, S and F; or
R$^{20}$ and R$^{21}$ form together with the atoms to which they are bound a fused, saturated or unsaturated alicyclic ring system with 4 to 12 carbon atoms or a fused aromatic ring system with 6 to 12 carbon atoms, which, for its part, can be substituted by C$_1$-C$_6$ alkyl or benzyl;
R$^{22}$=n-times substituted C$_1$- to C$_{10}$ alkylene, C$_6$- to C$_{10}$ arylene, —O—C(=O)-phenylene-C(=O)—O—, (—C(=O)—)$_4$(C$_6$H$_2$), 2,4,6-trioxo-1,3,5-triazinyl, —O—C(=O)—(CH$_2$)$_m$—C(=O)—O—; —O—C(=O)—NH—(CH$_2$)$_m$—NH—C(=O)—O—, m being an integer from 1 to 10;
n=an integer from 1 to 4.

In the case of the groups A' and A'' the number of heteroatoms is preferably 10 at most, provided that the above definitions permit such a number of carbon atoms and heteroatoms.

The carbon atoms and heteroatoms of A' and A'' can form 1 to (u−1) carbonyl groups. The maximum number of carbonyl groups is preferably 5 at most, provided that the above definitions permit such a number of carbon atoms and heteroatoms.

In the case of the groups R$^{20}$ and R$^{22}$ the number of heteroatoms is preferably 20 at most, provided that the above definitions permit such a number of carbon atoms and heteroatoms.

The carbon atoms and heteroatoms of R$^{20}$, R$^{21}$ can form 1 to (v−1) carbonyl groups. The maximum number of carbonyl groups is preferably 10 at most, provided that the above definitions permit such a number of carbon atoms and heteroatoms.

Preferred definitions for the individual variables, which can be selected independently of each other, are:
A', A''=—CH$_2$—;
B=—CH$_2$— or is absent;
R$^{20}$, R$^{21}$=H, —C(=O)—OCH$_3$; —O—C(=O)—CH$_3$; —CH$_2$—O—C(=O)—CH$_3$; or
R$^{20}$ and R$^{21}$ form together with the atoms to which they are bound a fused, saturated or unsaturated alicyclic ring system with 5 to 7 carbon atoms or an oxygen-containing heterocycle with 4 carbon atoms and an oxygen atom, which is unsubstituted or can be substituted by =O, such as for example a fused lactone ring;
R$^{22}$=1- to 3-times substituted C$_1$- to C$_6$ alkylene, in particular C$_1$- to C$_3$ alkylene; —O—C(=O)-phenylene-C(=O)—O—, —O—C(=O)—(CH$_2$)$_m$—C(=O)—O—; —O—C(=O)—NH—(CH$_2$)$_m$—NH—C(=O)—O—, m being an integer from 1 to 6;
n=an integer from 1 to 3.

Quite particularly preferred monomers are:

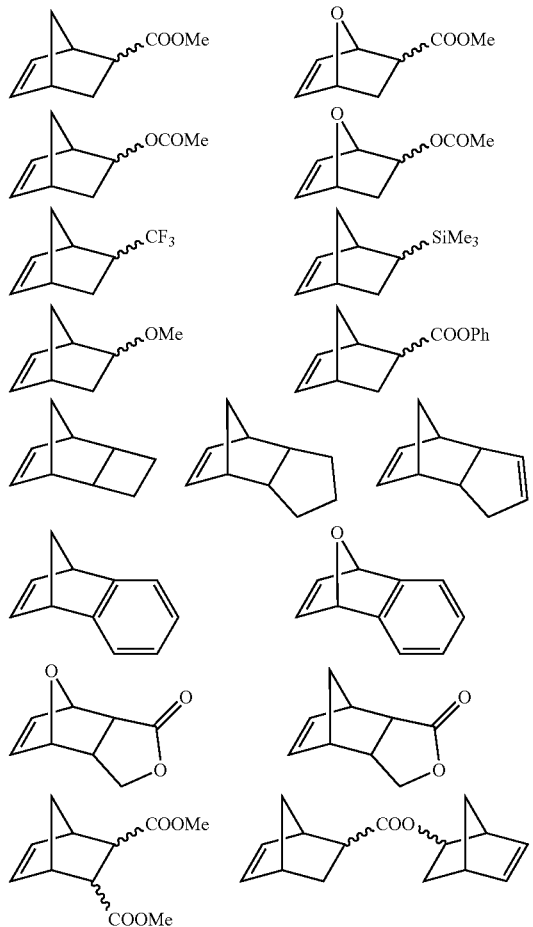

-continued

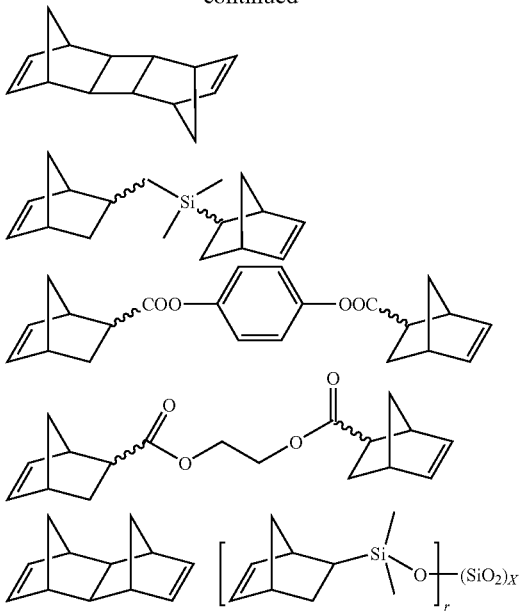

Moreover, oligomeric compounds with groups capable of metathesis can be used as component (a). To be named here in particular are oligomers of norbornene derivatives which, along with the norbornene group, carry an oligomeric radical with a numerically average molar mass of 200 to 10000 g/mol. The norbornene radicals can be unsubstituted or substituted by $C_{1-10}$ alkyl, phenyl and/or $C_{1-5}$ carboxylic acid —$C_{1-10}$ alkylester groups.

Particularly preferred oligomers are:

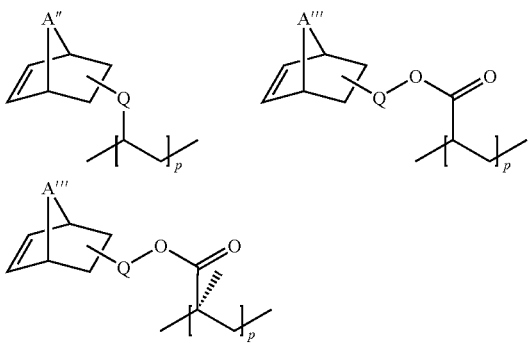

with
p=3 to 100
A'''=O, $CH_2$, S, NH
Q=$C_1$-$C_{20}$ alkylene, with 0-3 heteroatoms of the group N, O, Si, P, S and 0-2 carbonyl groups as spacer.

The bond of Q to the norbornene radical can take place via positions 1, 4, 5, 6 or 7.

According to the invention the filler acts as a support of the initiator and preferably also as a multifunctional and thus crosslinking component, i.e. it can be incorporated into the polymer or polymer network via free active groups not charged with initiator. When using crosslinking fillers and in particular when using crosslinking fillers and covalently bound initiators, it transpires that even materials based on monomers with only one norbornene group after curing contain practically no, or only small, portions which can be dissolved out with suitable organic solvents.

The choice of solvent is dependent on the monomer, in the dissolution test a solvent should be used in which a homopolymer from the monomer used is soluble. A solvent which can often be used is dichloromethane. The compositions according to the invention preferably contain after curing less than 10 wt.-%, relative to the overall mass, of portions dissolved out with dichloromethane.

A major problem with the preparation of materials which can be cured by ROMP is the poor solubility of the ROMP-initiators in the various known liquid monomers. According to the state of the art the initiators are dispersed in the composition. A consequence of this is that a significant share of the initiator used, namely that in the inside of the initiator particles, is not monomer-accessible, consequently cannot initiate a polymerization and thus is not effective. As the initiators are in most cases intensely-coloured compounds, still-unreacted initiator particles and initiator agglomerates can even be recognized by the naked eye in the finished shaped part.

The fixing according to the invention of the initiator to the filler results in a quasi-monomolecular distribution of the initiator on the surface of the filler, and all of the initiator used is monomer-accessible. Through the support-fixing of the initiator the initiator efficiency can be significantly increased or, put another way, in order to achieve the same result in the mechanical properties, less initiator needs to be used. Moreover, an improved distribution of the initiator in the composition is achieved, so that a more homogeneous curing and thus more uniform mechanical properties are achieved.

A decisive advantage for dental applications is in addition that, through the binding of the initiator to the filler surface, discolorations of the material by the initiator can be avoided. Through the support-fixing of the initiator practically colourless and tooth-coloured composites can be prepared.

Further components (d) above all stabilizers, UV-absorber, dyes, pigments and/or lubricants, can be added to the dental materials according to the invention if need be. The share of these further components is preferably in each case in the range from 0 to 1 wt.-% and particularly preferably 0 to 0.2 wt.-%.

The compositions according to the invention are preferably solvent-free. By solvents are meant here substances liquid at room temperature which serve alone to implement management of the reaction or facilitate handling without being still present or necessary in the finished cured composition. Liquid monomers (a) are consequently not solvents in this sense.

The compositions according to the invention are particularly suitable as dental materials, in particular dental prosthesis plastics for the preparation of false teeth and dental restorations, as facing materials or filler materials.

To prepare for example prostheses or false teeth the compositions are transferred into suitable polymerization moulds and cured there.

Thus for example, prostheses, teeth, inlays or facing materials which can be cured extraorally at 80 to 100° C. can be prepared based on thermally activatable initiators. Due to the hydrophobic properties of the formed composites these are characterized by an extremely low water absorption and film formation. With materials for the preparation of teeth and prosthesis materials, compared with inlay or facing materials, a clearly smaller portion of filler is used. Compositions according to the invention with a high filler portion based on photochemically activatable initiators are suitable in particular for use as direct filling material. These can be combined with thermally activatable initiators, so that a degree of precuring can be achieved initially through photochemically induced ROMP, and then the final curing takes place through a longer-lasting thermally induced ROMP at body temperature.

Compositions for use as dental materials contain the individual components preferably in the following proportions:
(i) 10 to 60 wt.-%, preferably 20 to 40 wt.-% and particularly preferably 20 to 40 wt.-% of at least one monomer/oligomer which is open to ring-opening metathesis polymerization, and
(ii) 5 to 90 wt.-% filler.

The given quantity of filler is the total quantity of filler, i.e. filler which is charged with an initiator for the ring-opening metathesis polymerization, and filler without initiator. Filler with initiator is preferably used in a quantity of 5-90 wt.-%, other fillers are preferably used in a quantity of 0 to 85 wt-%. The initiator content can be set on the one hand via the quantity of the filler charged with initiator and on the other hand via the charging of the filler with initiator. According to the invention, an initiator content in the whole composite of 0.001-0.1 wt.-%, in particular 0.01-0.08 wt.-% is preferred.

The quantity of filler is based on the desired use of the dental material. Composite cements preferably contain 40 to 70 wt.-% filler, composites, for example for inlays or for use as filler material preferably 50 to 85 wt.-%. Materials for the preparation of teeth and prostheses materials preferably contain 5 to 30 wt.-% filler.

All percentages relate, unless otherwise stated, to the overall mass of the composition.

The invention is explained in more detail in the following with reference to embodiments:

EXAMPLES

Beispiel 1: Surface Modification of Filler with Groups Capable of Metathesis

1a: Surface Modification of Pyrogenic $SiO_2$ by Means of Silanization 4.0 g pyrogenic $SiO_2$ (Aerosil OX50, Degussa) were weighed into a three-necked flask and thoroughly heated (as standard at 180-200° C., 5 h, in oil-pump vacuum accompanied by stirring). A heated-out reflux condenser was fitted on in $N_2$ countercurrent and the flask provided with a septum. The reflux condenser was connected to a thermostatting unit, the temperature of which was set at 90° C., so that the alcohol (ethanol) split off in the course of the silanization is condensed, not in the cooler but only in the water-cooled destination bridge fitted onto it and thus removed from the equilibrium. The filler was suspended in 50 ml abs. xylene, 2.564 g (10 mmol) of the silanization agent norborn-2-ene-5-yl-triethoxysilane added and the reaction mixture stirred for 6 h at 140° C. under nitrogen. The cooled solution was centrifuged, the silanized filler washed 3 times with abs. dichloromethane and dried under vacuum at 40° C. overnight. The norbornenyl groups content was able to be determined via C,H elemental analysis (0.849% C and 0.200% H) at 0.101 mmol/g filler.

1b: Surface Modification of a Glass Filler by Means of Silanization

Analogously to Example 1a 4.0 g of a barium silicate glass (GM27884, Schott Werke) were thoroughly heated, suspended in 50 ml abs. xylene and reacted with 2.564 g (10 mmol) of the silanization agent norborn-2-ene-5-yl-triethoxysilane and the reaction mixture stirred for 6 h at 140° C. under nitrogen. The cooled solution was centrifuged, the silanized filler washed 3 times each with 50 ml abs. dichloromethane and dried under vacuum at 40° C. overnight. The norbornenyl groups content was determined via C,H-elemental analysis (0.244% C and 0.155% H) at 0.029 mmol/g filler.

Example 2

Immobilization of Initiator on Surface-Modified Filler

2a: Immobilization of the Metathesis Initiator $Cl_2(PCy_3)_2Ru$=CHPh Active at Room Temperature The immobilization of the metathesis initiator $Cl_2(PCy_3)_2Ru$=CHPh was carried out in a glovebox under nitrogen atmosphere. 1.2 g of the filler prepared in Example 1b, surface-modified with norbornenyl groups, were suspended in 2.86 ml of a solution of $Cl_2(PCy_3)_2Ru$=CHPh in abs. dichloromethane of the concentration 0.5 mg/ml and stirred at room temperature for one hour. The supernatant of the suspension was colourless. Approx. 6% of the norbornenyl groups of the surface-modified filler were covalently charged with initiator. The reactive filler charged with initiator was centrifuged off from the solvent, dried for 2 hours under oil-hydraulic vacuum and then stored deep-cooled.

2b: Immobilization of the Thermally Activatable Initiator $RuCl_2(CHCH_2CH_2$—$C,N$-2-$C_5H_4N)(PiPr_3)$ 0.608 g of the filler prepared in Example 1b, surface-modified with norbornenyl groups, were suspended in a solution of 1.8 mg (0.0029 mmol) $RuCl_2(CHCH_2CH_2$—$C,N$-2-$C_5H_4N)(PiPr_3)$ in 3 ml abs. dichloromethane. The solvent was drawn off on a rotary evaporator. The initiator was adsorptively bound to the filler surface. The charging of the filler with initiator was 0.0048 mmol initiator/g filler.

Example 3

Polymerization and Preparation of Composite Shaped Parts

3a: ROMP of endo-,exo-(bicyclo[2.2.1]hept-5-en)-2-carboxylic Acid Methylester (BCHCM) in the Presence of an Initiator Active at Room Temperature ($Cl_2(PCy_3)_2Ru$=CHPh)

320 mg of the initiating filler described in Example 2a, and 280 mg of the surface-modified filler described in Example 1b were intimately mixed with 320 mg BCHCM at room temperature (degree of fill: 65.2 wt.-%, monomer/initiator-ratio=4530) and immediately transferred into forms for testing bending strength (25×2×2 mm). Curing took place at 80° C. over a period of 20 h. The thoroughly cured material showed a bending E modulus of 5780 MPa and was cream-coloured. The extraction of the shaped part with 7.5 g dichloromethane (room temperature, 5 days), which is a solvent for poly(B-CHCM), showed that the testpieces remained dimensionally stable. 0.42 wt.-% of unreacted monomer (relative to the quantity of monomer used), as well as 9.13 wt.-% of polymer ($M_n$=5390 g/mol, $M_w$=16600 g/mol, PDI=3.1), relative to the overall weight (that is 26.24 wt-% relative to the quantity of monomer used) could be extracted.

Further tests were carried out (cf. Table 1), which showed that the initiator content can be reduced by admixing a reactive filler according to Example 1b without thereby causing the mechanical properties to deteriorate, but with increasingly "more colourless" products being obtained. The initiator was charged analogously to Example 2a with the quantities of initiator stated in Table 1.

was not able to be distributed finely enough, agglomerates of the initiator molecules were present, of which only the mol-

TABLE 1

Properties of ROMP products with initiators active at room temperature

| Filler acc. to 2a [mg] | Immob. initiator [mg/gFS][1] | Filler acc. to 1b [mg] | Monomer [mg] | Initiator content[2] [wt. %] | Degree of fill [%] | Monomer/ initiator[3] | E-Modulus [Mpa][4] | Colour |
|---|---|---|---|---|---|---|---|---|
| 393 | 2.16 | 0 | 391 | 0.108 | 50.1 | 2487 | 3450 | caramel |
| 362 | 2.03 | 40 | 405 | 0.091 | 49.8 | 2983 | 3570 | light caramel |
| 307 | 2.03 | 91 | 403 | 0.078 | 49.7 | 3501 | 2970 | light caramel |
| 262 | 2.03 | 144 | 406 | 0.066 | 50.0 | 4132 | 3260 | light caramel |
| 404 | 0.9 | 0 | 405 | 0.045 | 49.9 | 6015 | 3860 | cream-coloured |
| 262 | 0.9 | 40 | 301 | 0.039 | 50.1 | 6893 | 3430 | cream-coloured |
| 288 | 0.9 | 112 | 400 | 0.032 | 50.0 | 8333 | 3220 | cream-coloured |

[1]metathesis initiator immobilized on filler in mg initiator per gram of filler (FS) acc. to 2a
[2]initiator content relative to the overall weight of the composite
[3]molar ratio monomer/initiator
[4]bending E modulus determined according to EN 24 049 / ISO 4049

3b: ROMP of BCHCM in the Presence of a Physically Bound Metathesis Initiator ($Cl_2(PCy_3)_2Ru=CHPh$)

1.0 g of a glass filler (GM27884, Schott Werke) surface-modified with γ-methacryloxypropyltrimethoxysilane was suspended in a solution of 0.64 mg $Cl_2(PCy_3)_2Ru=CHPh$ in 1 ml abs. dichloromethane. The solvent was drawn off in vacuum. 601 mg of this inert filler charged with metathesis initiator were intimately mixed with 320 mg BCHCM at room temperature (degree of fill: 65.3%, monomer/initiator ratio=4499) and immediately transformed into forms for testing bending strength. The material cured analogously to 3a showed a bending E modulus of 5440 MPa and was cream-coloured. If the shaped part was extracted in 7.5 g dichloromethane (room temperature, 5 days), it completely dissolved, the filler sank to the bottom, the supernatant solution was coloured light violet brown by the initiator. The dissolved poly(BCHCM) was able to be precipitated in methanol.

3c: ROMP of BCHCM in the Presence of Non-Filler-Bound Initiator (Comparison Example)

The metathesis initiator was admixed in conventional manner to the mass to be polymerized. 0.19 mg $Cl_2(PCy_3)_2Ru=CHPh$ was weighed in onto a watch glass. To achieve a fine distribution of the initiator the corresponding quantity of a solution of the metathesis initiator in dichloromethane (0.5 mg/ml) was applied and the solvent left to evaporate slowly. 300 mg of the surface-modified filler described in Example 1b and 160 mg BCHCM were intimately mixed with the initiator (degree of fill 65.2%, monomer/initiator=4499). The material cured analogously to 3a showed a bending E modulus of 5030 MPa. In Table 2 results of further tests are listed which show that, already with a monomer/initiator ratio of 6200 (initiator content in the composite:0.044 wt %), shaped parts can no longer be prepared anymore. The reason for this is the poor solubility of the initiator in the liquid BCHCM. The initiator ecules at the surface can initiate a polymerization. Thus the effectively active quantity of initiator was too small to fully cure the dental composition.

According to the results shown in Table 1 the materials according to the invention were still able to be cured with a monomer/initiator ratio of 8333 (corresponds to an initiator content of 0.03 wt.-%) to produce cream-coloured shaped parts. The compositions according to the invention also displayed mechanical properties which in the case of conventional materials can be achieved only with very much greater quantities of initiator, i.e. at a lower monomer-to-initiator ratio.

In analogously conducted tests, shaped parts with comparable mechanical properties with an initiator content of 0.02 wt.-% could be prepared.

TABLE 2

Properties of ROMP products with conventional initiators

| Initiator [mg][1] | Filler acc. to 1b [mg] | Monomer [mg] | Initiator content[2] [wt %] | Degree of fill [%] | Monomer/ initiator[3] | E-Modulus[4] [Mpa] | Colour |
|---|---|---|---|---|---|---|---|
| 0.36 | 202 | 208 | 0.088 | 49.27 | 3124 | 3480 | beige |
| 0.18 | 201 | 208 | 0.044 | 49.14 | 6249 | —[5] | — |

[1]mg per admixed initiator 1
[2]initiator content relative to the overall weight of the composite
[3]Molar ratio monomer/initiator
[4]bending E modulus determined according to EN 24 049 / ISO 4049
[5]The mixture of this composition did not cure, thus no shaped parts could be obtained.

3d: ROMP of BCHCM in the Presence of a Thermally Switchable Metathesis Initiator ($RuCl_2(=CHCH_2CH_2$—$C,N$-$2$-$C_5H_4N)(PiPr_3)$)

183.5 mg of the reactive filler prepared in Example 2b charged with the thermally switchable metathesis initiator, were intimately mixed with 184.8 mg BCHCM at room temperature (degree of fill 49.8%, monomer/initiator ratio=1370) and immediately transformed into a form for testing bending strength. By increasing the temperature to 100° C., the initiator was activated and the metathesis polymerization started. The reaction time was 2 h. The thoroughly cured material showed a bending E modulus of 4370 MPa. Through partial substitution of the initiating filler by the surface-modified reactive filler the effective initiator content of the composites was progressively reduced, while maintaining or improving the mechanical properties (cf. Table 3). As the degree of fill increased and the initiator content fell the testpieces became increasingly "more colourless".

TABLE 3

Properties of ROMP-products with thermally activatable initiators

| Filler acc. to 2b [mg] | Initiator [mg/gFS][1] | Filler acc. to 1b [mg] | Monomer [mg] | Initiator content [wt %][2] | Degree of fill [%] | Monomer/ initiator[3] | E-Modulus [MPa][4] | Colour |
|---|---|---|---|---|---|---|---|---|
| 91 | 2.96 | 110 | 209 | 0.066 | 49.02 | 3133 | 3830 | caramel |
| 37 | 2.96 | 166 | 202 | 0.027 | 51.54 | 7448 | 4370 | cream |

[1] quantity of initiator in mg adsorbed per g of filler (FS) according to 2b
[2] initiator content relative to the overall weight of the composite
[3] molar ratio monomer/initiator
[4] bending E modulus determined according to EN 24 049 / ISO 4049

The invention claimed is:

1. Dental composition containing
   (a) 10 to 60 wt.-% of at least one monomer and/or oligomer which is polymerizable by ring-opening metathesis polymerization,
   (b) 5 to 90 wt.-% of at least one particulate dental macro-filler or dental mini-filler having an average particle size of from 0.01 to 5 μm containing quartz, glass ceramic or glass powder, or at least one particulate dental microfine filler having an average particle size of from 0.005 to 0.5 μm containing pyrogenic silicic acid, or precipitated silicic acid, or a mixed oxide of at least one of $SiO_2$, $ZrO_2$, $TiO_2$, $TaO_2$, $La_2O_3$, $Yb_2O_3$ and $CeO_2$, or at least one X-ray opaque filler containing ytterbium trifluoride, and
   (c) 0.01 to 0.08 wt.-% of at least one initiator for ring-opening metathesis polymerization,
   characterized in that the initiator is chemically or physically bound to the filler and the composition is solvent-free, substantially colorless or tooth-colored and has properties suitable for use in a dental patient's mouth.

2. Composition according to claim 1, in which the initiator is chemically bound to the filler by a silane of formula (1):

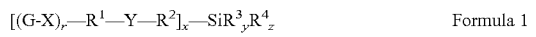

the variables of formula (1) having the following meanings:
   G=a linear or branched organic radical capable of metathesis with m carbon atoms, m being an integer from 1 to 40, and 0 to (m−2) heteroatoms, selected from N, O, Si, P and S, or
   a cyclic or polycyclic, cycloaliphatic or aromatic organic radical capable of metathesis with m' carbon atoms, m' being an integer from 3 to 63, and 0 to (m'−2) heteroatoms, selected from N, O, Si, P and S;
   X,Y=independently of each other —C(=O)—O—, —C(=O)—N—, —O—C(=O)—O—, —O—C (=O)—NR$^5$—, —CR$^5$=N—, —O—, —S—, with R$^5$=H, $C_1$-$C_6$-alkyl, benzyl or is absent;
   $R^1$=a (r+1)-valent, linear or branched aliphatic, cycloaliphatic or aromatic organic radical or is absent;
   $R^2$=a $C_1$-$C_5$ alkylene group or is absent;
   $R^3$=halogen, hydroxy, a $C_1$-$C_5$ alkoxy- or $C_1$-$C_5$ acyloxy group;
   $R^4$=$C_1$-$C_{12}$ alkyl, $C_3$-$C_{12}$ cyloalkyl or phenyl;
   r=1, 2 or 3;
   x=1, 2 or 3;
   y=1, 2 or 3;
   z=0, 1 or 2,
   the sum x+y+z is 4.

3. Composition according to claim 2, in which the variables of formula (1) have the following meaning:
   G=a radical of formula (2)

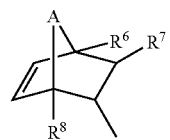

Formula (2)

in which the variables are defined as follows:
   A=O, NH, S, a saturated or unsaturated organic radical with t carbon atoms, t being an integer from 1 to 12, which can contain 0 to (t−1) heteroatoms, selected from N, O, Si, P and S;
   $R^6$, $R^7$, $R^8$=independently of each other in each case a linear or branched aliphatic radical with q carbon atoms, q being an integer from 1 to 15, a cyclic or polycyclic organic radical with q' carbon atoms, q' being an integer from 3 to 15, and 0 to (q−1) or 0 to (q'−1) heteroatoms, selected from N, O, Si, P, and S;
   X,Y=is absent;
   $R^1$=a linear $C_1$-$C_5$ alkyl radical or is absent;
   $R^2$=is absent;
   $R^3$=chlorine, methoxy, ethoxy;
   $R^4$=methyl;
   r=1;
   x=1;
   y=1, 2 or 3;
   z=0, 1 or 2.

4. Composition according to claim 1, in which the initiator is physically bound to the filler by a silane of formula (3):

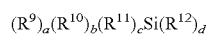

Formula (3)

$R^{12}$: halogen, hydroxy, a $C_1$-$C_5$ alkoxy- or $C_1$-$C_5$ acyloxy group;

$R^9$, $R^{10}$, $R^{11}$: independently of each other a saturated or unsaturated, linear or branched organic radical with s carbon atoms, s being an integer from 2 to 20, and 0 to (s−1) heteroatoms, selected from N, O, Si, P and S; or a saturated, unsaturated or aromatic, cyclic or polycyclic organic radical with s' carbon atoms, s' being an integer from 3 to 15, with 0 to (s'−1) heteroatoms, selected from N, O, Si, P and S;

a=0, 1, 2 or 3;
b=0, 1, 2 or 3;
c=0, 1, 2 or 3;
d=1, 2 or 3,
the sum of a+b+c+d being 4.

5. Composition according to claim 1, in which the initiator is an initiator active at room temperature.

6. Composition according to claim 5, in which the initiator is a compound of formula (4):

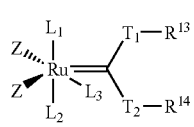

Formula 4

Z=Cl, Br, F, I, tosylate or one of the meanings given for $L_1$, $L_2$, $L_3$;

$L_1$, $L_2$, $L_3$=independently of each other $P(R^{15})_3$ with $R^{15}$=phenyl, isopropyl, cyclohexyl or

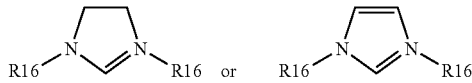

with $R^{16}$=mesityl (2,4,6-trimethylphenyl; MES); or pyridine which is unsubstituted or substituted in position 2 or in positions 2 and 4 with Br, Cl, F, I, $OCH_3$; or is absent;

$R^{13}$, $R^{14}$=independently of each other H or an aromatic or aliphatic, polycyclic or condensed $C_6$-$C_{20}$ ring or ring system, with 0-5 heteroatoms in the ring, selected from N, S, O, P, the ring or the ring system being unsubstituted or being substituted with 0-5 substituents selected from —Cl, —Br, —I, —F, —$OR^{17}$, —CH=N—$R^{17}$, —C(=O)$R^{17}$, —C(=O)O$R^{17}$, —OC(=O)$R^{17}$, $R^{17}$ being a linear or branched, acyclic $C_1$-$C_{14}$ alkyl or cyclic $C_3$-$C_{14}$ alkyl or an aromatic radical with 6 to 14 carbon atoms, $R^{17}$ being able to contain 0 to 5 heteroatoms, selected from N, O, Si, S;

$T_1$, $T_2$=independently of each other —O—, —S—, or a saturated or unsaturated $C_1$ to $C_4$ alkylene, which can additionally contain 0-2 heteroatoms of the group N, O, S, Si or is absent.

7. Composition according to claim 1, in which the initiator is a thermally or photochemically activatable initiator.

8. Composition according to claim 7, in which the initiator is

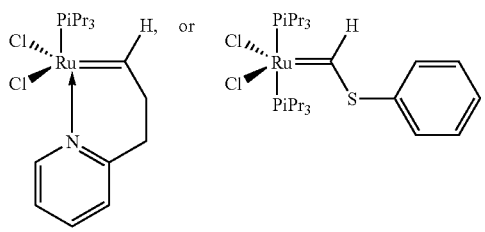

a compound of formula (5):

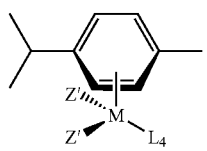

Formula 5

M=Os or Ru;
Z'=Cl, Br, F, I, tosylate or one of the meanings given for $L_4$;
$L_4$=P($R^{18}$)$_3$ with $R^{18}$=phenyl, isopropyl, cyclohexyl or

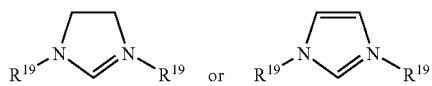

with $R^{19}$=mesityl (2,4,6-trimethylphenyl).

9. Composition according to claim 1, in which the filler is charged with 0.00001 to 0.1 mmol initiator per gram of filler.

10. Composition according to claim 1 which contains a second filler component which is surface-modified with a silane of formula (1).

11. Composition according to claim 1 which contains as component (a) at least one bi- or multicyclic ring compound with at least one endocyclic double bond.

12. Composition according to claim 11 which contains a carbocyclic or heterocyclic bicyclo[x'.y'.z']hydrocarbon, x', y' and z' independently of each other each being an integer from 1 to 6.

13. Composition according to claim 12 which contains a norbornene derivative of formula (6) and/or (7)

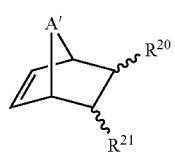

Formula (6)

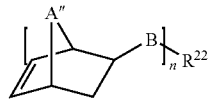

Formula (7)

in which the variables have the following meanings:

A', A"=O, S, NH, a saturated or unsaturated organic radical with u carbon atoms, u being an integer from 1 to 15, which can contain 0 to (u−1) heteroatoms, selected from N, O, Si, P and S;

B=—CH$_2$— or is dispensed with;

R$^{20}$, R$^{21}$=H or a saturated or unsaturated organic radical with v carbon atoms, v being an integer from 1 to 30, and with 0 to (v−1) heteroatoms from the group N, O, Si, P, S and F; or R$^{20}$ and R$^{21}$ form together with the atoms to which they are bound a fused, saturated or unsaturated alicyclic ring system with 4 to 12 carbon atoms or a fused aromatic ring system with 6 to 12 carbon atoms, which for its part can be substituted by C$_1$-C$_6$ alkyl or benzyl;

R$^{22}$=n-times substituted C$_1$- to C$_{10}$ alkylene, C$_6$- to C$_{10}$ arylene, —O—C(=O)-phenylene-C(=O)—O—, (—C(=O)—)$_4$(C$_6$H$_2$),2,4,6-trioxo-1,3,5-triazinyl, —O—C(=O)—(CH$_2$)$_m$—C(=O)—O—; —O—C(=O)—NH—(CH$_2$)$_m$—NH—C(=O)—O—, m being an integer from 1 to 10;

n=an integer from 1 to 4.

14. Composition according to claim 1, which further contains (d) at least one additive from the group stabilizer, UV-absorber, dye, pigment, lubricant.

15. Kit for the preparation of a dental composition containing
(a) 10 to 60 wt.-% of at least one monomer and/or oligomer which is polymerizable by ring-opening metathesis polymerization,
(b) 5 to 90 wt.-% of at least one particulate dental macro-filler or dental mini-filler having an average particle size of from 0.01 to 5 μm containing quartz, glass ceramic or glass powder or, at least one particulate dental microfine filler having an average particle size of from 0.005 to 0.5 μm containing pyrogenic silicic acid, or precipitated silicic acid, or a mixed oxide of at least one of SiO$_2$, ZrO$_2$, TiO$_2$, TaO$_2$, La$_2$O$_3$, Yb$_2$O$_3$ and CeO$_2$, or at least one X-ray opaque filler containing ytterbium trifluoride, and
(c) 0.01 to 0.08 wt.-% of at least one initiator for ring-opening metathesis polymerization, characterized in that the initiator is chemically or physically bound to the filler and the composition is solvent-free, substantially colorless or tooth-colored and has properties suitable for use in a dental patient's mouth, which contains the monomer/oligomer (a) and initiator-containing filler in physically separated form.

16. A method for the preparation of prostheses plastics or false teeth, comprising applying a dental composition containing
(a) 10 to 60 wt.-% of at least one monomer and/or oligomer which is polymerizable by ring-opening metathesis polymerization,
(b) 5 to 90 wt.-% of at least one particulate dental macro-filler or dental mini-filler having an average particle size of from 0.01 to 5 μm containing quartz, glass ceramic or glass powder or, at least one particulate dental microfine filler having an average particle size of from 0.005 to 0.5 μm containing pyrogenic silicic acid, or precipitated silicic acid, or a mixed oxide of at least one of SiO$_2$, ZrO$_2$, TiO$_2$, TaO$_2$, La$_2$O$_3$, Yb$_2$O$_3$ and CeO$_2$, or at least one X-ray opaque filler containing ytterbium trifluoride, and
(c) 0.01 to 0.08 wt.-% of at least one initiator for ring-opening metathesis polymerization, characterized in that the initiator is chemically or physically bound to the filler and the composition is solvent-free, substantially colorless or tooth-colored and has properties suitable for use in a dental patient's mouth, as facing material or filling material.

* * * * *